United States Patent
Long

(10) Patent No.: US 11,446,153 B2
(45) Date of Patent: Sep. 20, 2022

(54) TALAR IMPLANT SYSTEM AND METHOD

(71) Applicant: DePuy Synthes Products, Inc., Raynham, MA (US)

(72) Inventor: Jack F. Long, Warsw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 475 days.

(21) Appl. No.: 16/510,104

(22) Filed: Jul. 12, 2019

(65) Prior Publication Data
US 2019/0328538 A1 Oct. 31, 2019

Related U.S. Application Data

(62) Division of application No. 11/904,079, filed on Sep. 26, 2007, now Pat. No. 10,398,561.

(51) Int. Cl.
A61F 2/42 (2006.01)
A61F 2/46 (2006.01)
A61F 2/30 (2006.01)

(52) U.S. Cl.
CPC .......... *A61F 2/4202* (2013.01); *A61F 2/4606* (2013.01); *A61F 2002/30387* (2013.01); *A61F 2002/30616* (2013.01); *A61F 2002/4207* (2013.01)

(58) Field of Classification Search
CPC .......... A61F 2/4606; A61F 2002/30387; A61F 2/4202; A61F 2002/30616; A61F 2002/30649; A61F 2002/30538
See application file for complete search history.

(56) References Cited

U.S. PATENT DOCUMENTS

| | | | |
|---|---|---|---|
| 3,886,599 | A | 6/1975 | Schlein |
| 4,001,896 | A | 1/1977 | Arkangel |
| 4,021,864 | A | 5/1977 | Waugh |
| 4,069,518 | A | 1/1978 | Groth, Jr. et al. |
| 4,450,591 | A | 5/1984 | Rappaport |
| 4,470,158 | A | 9/1984 | Pappas et al. |
| 4,968,316 | A | 11/1990 | Hergenroeder |
| 5,073,110 | A | 12/1991 | Barbone |

(Continued)

FOREIGN PATENT DOCUMENTS

| | | |
|---|---|---|
| DE | 10 123 124 | 12/2002 |
| EP | 0 864 305 | 9/1998 |

(Continued)

OTHER PUBLICATIONS

"Total Replacement of the Ankle," G. Lord and J.H. Marotte (Paris), Revue de Chirurgie Orthopedique, 1973, 59, 139-151.

(Continued)

*Primary Examiner* — Brian E Pellegrino
(74) *Attorney, Agent, or Firm* — Maginot, Moore & Beck LLP

(57) ABSTRACT

A talar implant system and method in one embodiment includes an articulation component with an articulating surface extending upwardly from a first plane and configured to articulate with a tibial component, and a distal portion for implanting in a bone, the distal portion having a longitudinal axis and configured to be rigidly coupled with respect to the first plane at any angular position selected from a range of angular positions within a second plane perpendicular to the first plane.

11 Claims, 5 Drawing Sheets

(56) References Cited

U.S. PATENT DOCUMENTS

| | | |
|---|---|---|
| 5,201,769 A | 4/1993 | Schultzer |
| 5,207,712 A | 5/1993 | Cohen |
| 5,326,365 A | 7/1994 | Alvine |
| 5,360,450 A | 11/1994 | Giannini |
| 5,766,259 A | 6/1998 | Sammarco |
| 6,183,519 B1 | 2/2001 | Bonnin et al. |
| 6,197,029 B1 | 3/2001 | Fujimori et al. |
| 6,663,669 B1 | 12/2003 | Reiley |
| 6,673,116 B2 | 1/2004 | Reiley |
| 6,860,902 B2 | 3/2005 | Reiley |
| 6,863,691 B2 | 3/2005 | Short et al. |
| 6,875,236 B2 | 4/2005 | Reiley |
| 6,926,739 B1 | 8/2005 | O'Connor et al. |
| 6,939,380 B2 | 9/2005 | Guzman |
| 7,011,687 B2 | 3/2006 | Deffenbaugh et al. |
| 2003/0040802 A1* | 2/2003 | Errico ................ A61F 2/4425 623/17.14 |
| 2004/0064188 A1* | 4/2004 | Ball ................... A61F 2/4014 623/19.11 |
| 2004/0078078 A1 | 4/2004 | Shepard |
| 2005/0075735 A1 | 4/2005 | Berelsman et al. |
| 2005/0124995 A1 | 6/2005 | Reiley |
| 2005/0125070 A1 | 6/2005 | Reiley |
| 2005/0288792 A1 | 12/2005 | Landes et al. |
| 2006/0009845 A1 | 1/2006 | Chin |
| 2006/0229730 A1 | 12/2006 | Railey et al. |
| 2007/0150065 A1 | 6/2007 | Angibaud |

FOREIGN PATENT DOCUMENTS

| | | |
|---|---|---|
| FR | 2 220 235 | 10/1974 |
| FR | 2 543 821 | 10/1984 |
| FR | 2 615 726 | 12/1988 |
| FR | 2 680 968 | 12/1993 |
| FR | 2 700 462 | 7/1994 |
| GB | 2 297 257 | 7/1996 |
| WO | 9107931 | 6/1991 |
| WO | 2001030264 | 5/2001 |
| WO | 2006099270 | 9/2006 |

OTHER PUBLICATIONS

European Patent Office, European Search Report, Application—EP 08 16 5073, dated Jan. 22, 2009 (2 pages).

* cited by examiner

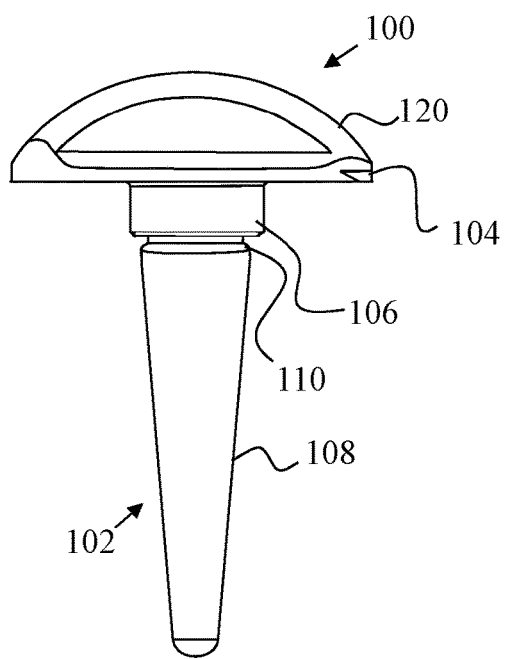
FIG. 1
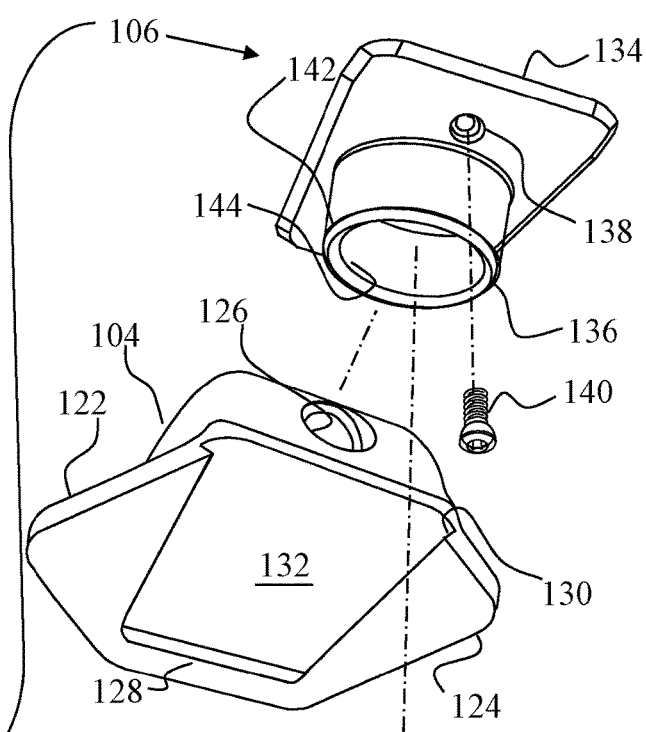
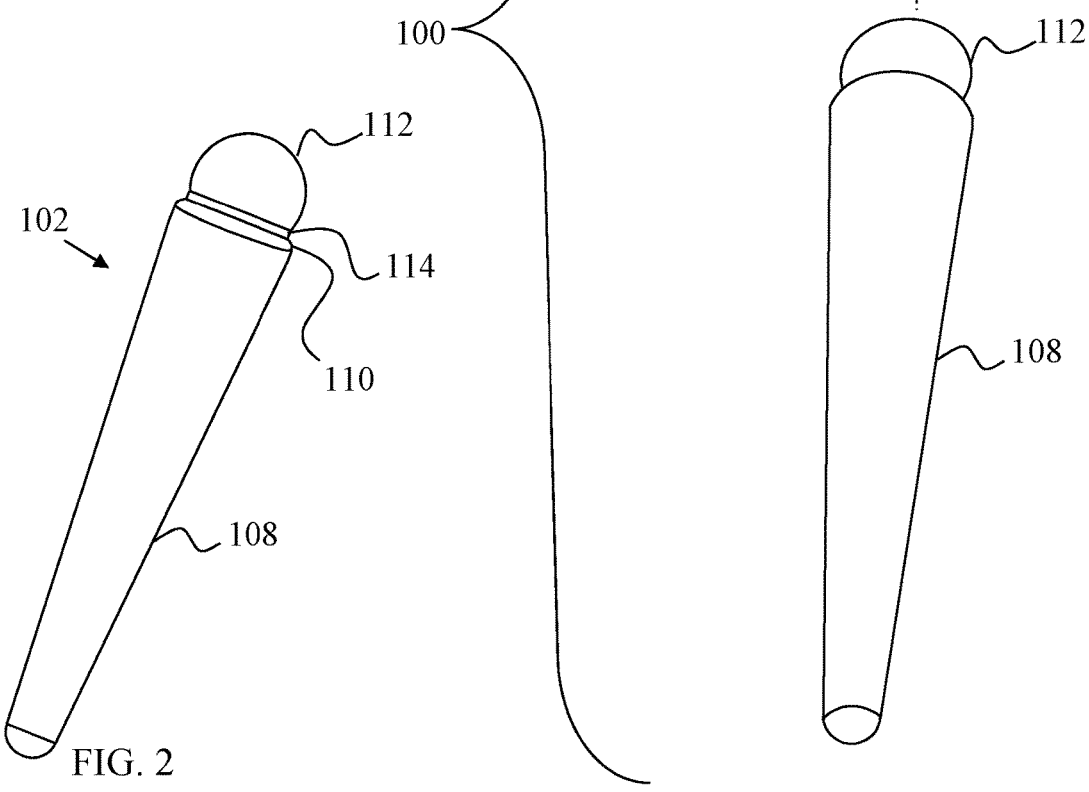
FIG. 2
FIG. 3

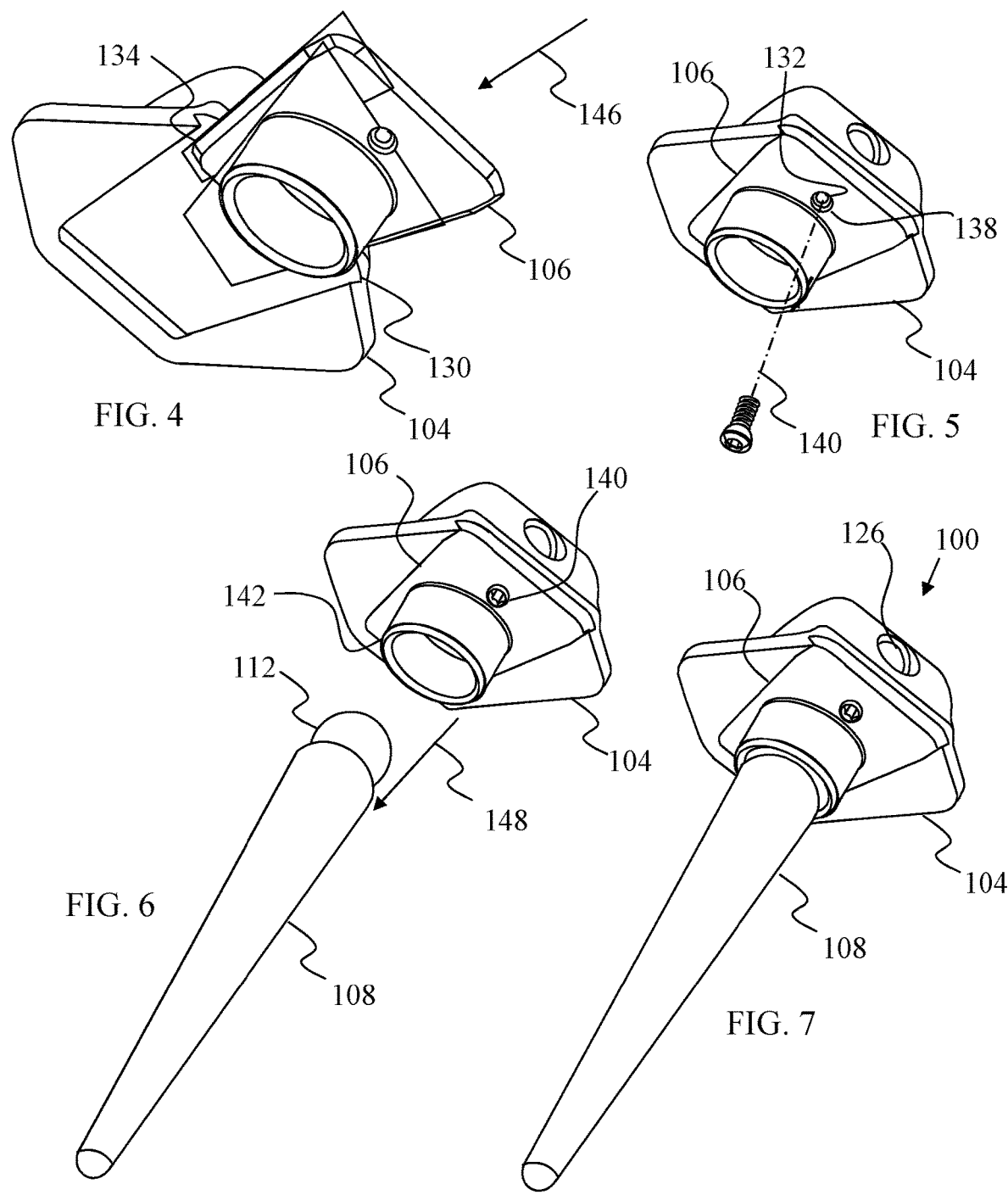

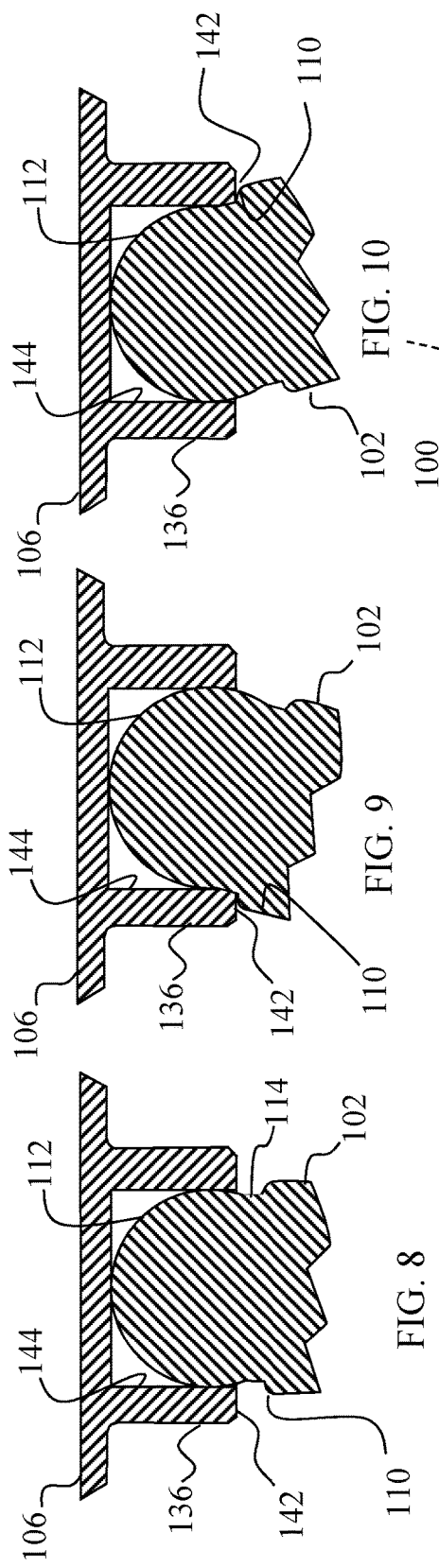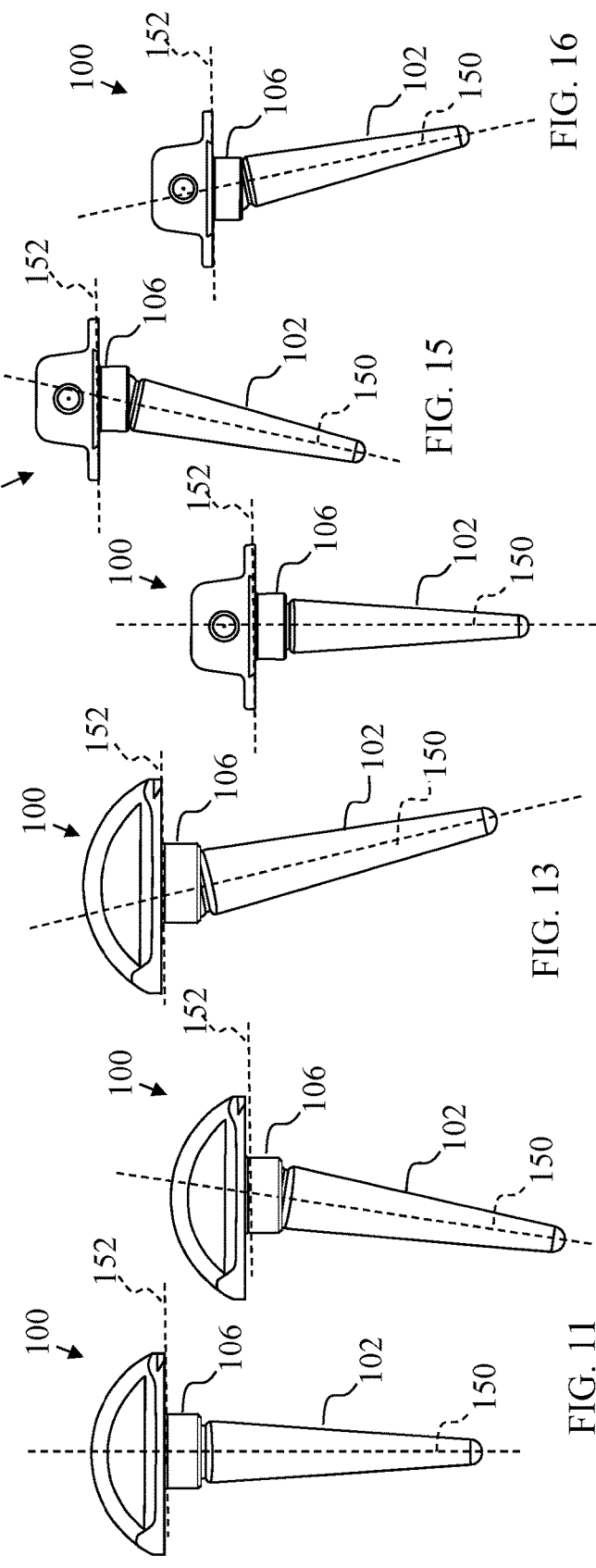

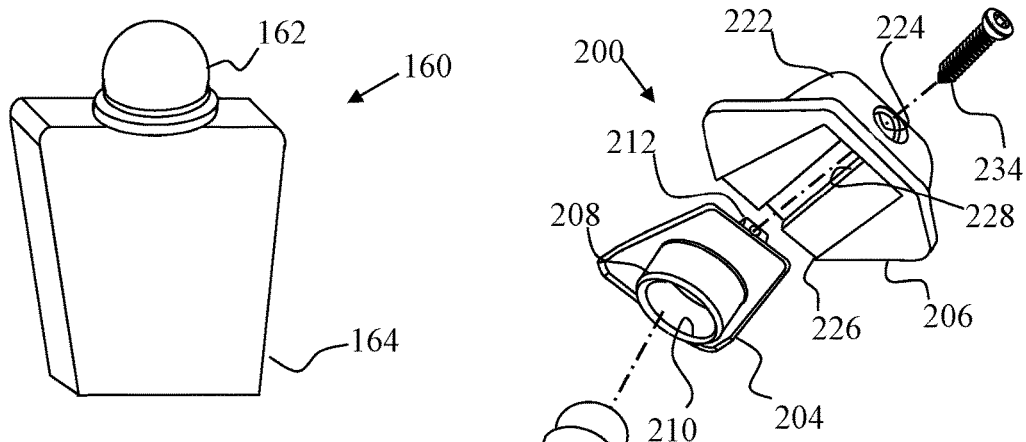
FIG. 17
FIG. 18
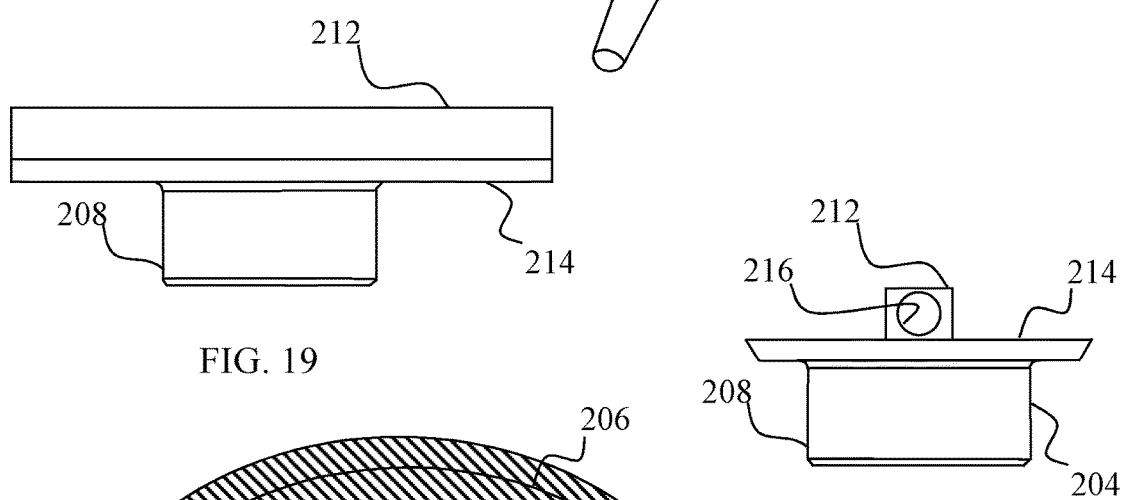
FIG. 19
FIG. 20
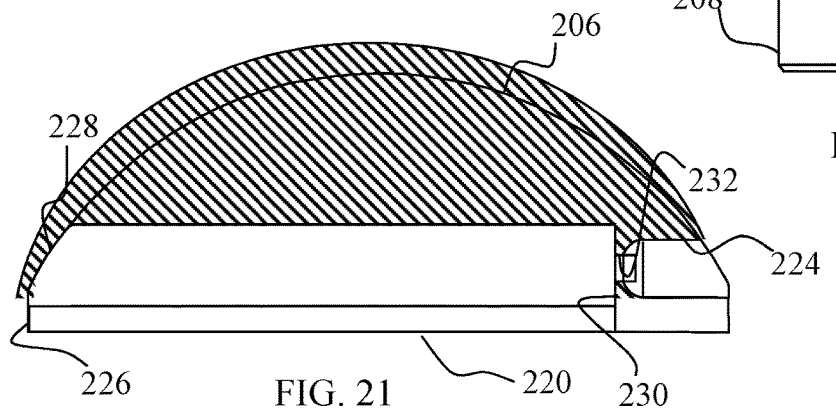
FIG. 21

TALAR IMPLANT SYSTEM AND METHOD

This application is a divisional of co-pending application Ser. No. 11/904,079, filed on Sep. 26, 2007, which issued as U.S. Pat. No. 10,398,561 on Sep. 3, 2019 the disclosure which is hereby incorporated by reference in its entirety.

FIELD OF THE INVENTION

This invention relates to the field of orthopaedics and more particularly to methods and instrumentation used in orthopaedic procedures.

BACKGROUND

Prosthetic devices which are implanted for replacement of joints are well known. Such implants take the place of native joints. Implants may be used for patients suffering from rheumatism and degenerative or traumatic arthritis, including osteoarthritis. The ankle joint, or the joint between the tibia, fibula and the talus, is frequently a source of osteo or rheumatoid arthritis. Formerly, sufferers of rheumatoid or osteoarthritis at the ankle joint have been generally limited to a procedure called fusing. In a fusing procedure, the tibia, and typically the fibula, are fused or secured together with the talus to reduce the patient's pain and improve mobility. Of course, fusing a joint does not provide the same degree of motion as a joint which is not fused.

The design of a replacement joint, however, is complicated by various considerations. For example, the replacement joint should not occupy more space in the body than the natural joint. Additionally, the replacement joint must be connected with the bone and tissue remaining after surgery. Moreover, obtaining surgical access to the joint typically destroys some tissue which provides support for the native joint. Thus, a replacement joint must not only have sufficient strength and durability to withstand the weight and stresses which are applied to a native joint, the replacement joint must further be configured to withstand additional stresses not typically applied to a native component.

Ankle joints pose additional problems due to the shifting of weight and type of motion required for walking. Thus, matching the pivot point of the joint is critical, as misalignment can lead to difficulty in walking and other motions, which may cause the patient considerable pain.

The durability of a replacement joint is also important. The high stresses experienced by an ankle replacement during walking, running, and jumping, all of which are compounded over time, may crack or fracture ankle components of replacement joints, which absorb a substantial amount of the pressures during the aforementioned activities.

A particularly successful ankle implant for use in total ankle arthroscopy is disclosed in U.S. Pat. No. 5,326,365 to Alvine. The total ankle implant, as disclosed in U.S. Pat. No. 5,326,365, is marketed by DePuy Orthopaedics, Inc. under the name Agility™ Ankle. This type of ankle prosthesis performs quite well on patients having a primary or initial total ankle arthroplasty. Occasionally, however, the talus of the patient may be in such a condition that the talus does not provide sufficient support for the total ankle prosthesis.

When there is insufficient support for an ankle prosthesis, or as osteoarthritis or rheumatoid arthritis or aging progresses, a prosthesis may subside into the talus and may eventually pass through the talus into calcaneus. Additionally, the forgoing processes may results in aseptic loosening of the ankle prosthesis.

Loosened or subsided components may result in bone loss and cause severe pain to the patient. Additionally, subsidence of the ankle prosthesis may result in reduced motion of the ankle. For example, the loosening and the subsidence of an ankle prosthesis may result in loss of plantar flexion. Further subsidence and loosening of the ankle prosthesis may also limit the inversion and eversion movements of the ankle.

The loosening and subsidence of an ankle prosthesis usually occurs with massive bone loss to the talus and as stated earlier, the prosthesis may subside down into the calcaneus. The mere replacement of the original prosthesis with another larger component is generally is not successful in correcting the problem.

Attempts to address the revision of the total ankle arthroplasty have met with limited success. Once the primary ankle prosthesis has loosened and subsided, the typical surgical procedure is to fuse the ankle. In such a procedure a metal rod is inserted through the calcaneus through the talus into the tibia to fuse or lock the talus to the tibia.

With some very limited success, some failed primary total ankle arthroplasty prostheses have been replaced with a revision total ankle arthroplasty. The prosthesis for such procedures may need to be specially designed and specially built. These prostheses can be very specific expensive and provide the surgeon with only one very specific implant option in time of the surgery. Additionally, the implantation of such custom devices is often a very technically demanding procedure as instrumentation and surgical procedures are not well established.

Therefore, a need exists for an ankle prosthesis that provides improved support for a wide range of patient anatomies and disease states. A further need exists for an ankle prosthesis which is easily replaced when the articulating portion of the prosthesis becomes worn.

SUMMARY

A talar implant system and method in one embodiment includes an articulation component with an articulating surface extending upwardly from a first plane and configured to articulate with a tibial component, and a distal portion for implanting in a bone, the distal portion having a longitudinal axis and configured to be rigidly coupled with respect to the first plane at any angular position selected from a range of angular positions within a second plane perpendicular to the first plane.

In a further embodiment, a method of implanting a talar prosthesis includes coupling an articulation component having a surface configured to articulate with a tibial prosthetic device to a base member having a base plane, selecting an angular position from a set of potential angular positions, the set of potential angular positions including (i) a first potential angular position of the longitudinal axis of a distal portion with respect to the base plane, (ii) a second potential angular position of the longitudinal axis of the distal portion with respect to the base plane, and (iii) the range of angular positions between the first potential angular position and the second potential angular position along a first plane perpendicular to the base plane and including the first angular position and the second angular position, rigidly coupling a distal portion with the base member at the selected angular position, and implanting the distal portion in a bone.

In a further embodiment, a talar implant kit includes a plurality of articulation components, each of the plurality of articulation components having a surface configured to articulate with a tibial prosthetic device, a plurality of base members, each base member configured to couple with each of the plurality of articulation components and including a first coupling member, and a plurality of distal members, each distal member including a longitudinal axis and a second coupling member configured to couple with the first coupling member, the first coupling member and the second coupling member configured for coupling at any angular position within a cone having a vertex at the first coupler.

In yet another embodiment, a talar implant includes an articulation component with a first coupling portion and an articulating surface extending upwardly from a plane and configured to articulate with a tibial component, and a distal portion for implanting in a bone, the distal portion having a second coupling portion configured to frictionally couple with the first coupling portion by moving the second coupling portion along the first plane such that the distal portion extends downwardly from the plane.

BRIEF DESCRIPTION OF THE DRAWINGS

FIG. 1 depicts a side plan view of a talar implant in accordance with principles of the present invention;

FIG. 2 depicts a perspective view of the distal portion of the talar implant of FIG. 1;

FIG. 3 depicts a an exploded perspective view of the talar implant of FIG. 1;

FIG. 4 depicts a perspective view of the base component of FIG. 1 positioned for coupling with the articulating component of FIG. 1;

FIG. 5 depicts a perspective view of the base component of FIG. 1 coupled with the articulating component of FIG. 1 using a dovetail coupling and a fastener positioned to rigidly couple the base component with the articulating component;

FIG. 6 depicts a perspective view of the rigidly coupled base component and articulating component of FIG. 1 and the distal portion of FIG. 1 positioned to couple with the base component;

FIG. 7 depicts a perspective view of the talar implant of FIG. 1;

FIGS. 8-10 depict partial cross sectional views of the distal portion of FIG. 1 coupled with the base of FIG. 1 at different in accordance with principles of the present invention;

FIGS. 11-13 depict side plan views of the talar implant of FIG. 1 showing possible angular orientations of the distal portion within the base in an anterior/posterior plane in accordance with principles of the present invention;

FIGS. 14-16 depict side plan views of the talar implant of FIG. 1 showing possible angular orientations of the distal portion within the base in the medial/lateral plane in accordance with principles of the present invention;

FIG. 17 depicts an alternative embodiment of a distal portion that may be used with the base and articulating component of FIG. 1;

FIG. 18 depicts a side perspective view of an alternative talar implant including a guide in the base and a channel in the articulating component wherein a fastener is inserted into a bore in the guide through a bore between a tool coupler and the channel in accordance with principles of the present invention;

FIG. 19 depicts side plan view of the base of FIG. 18;

FIG. 20 depicts rear plan view of the base of FIG. 18;

FIG. 21 depicts a cross sectional view of the articulating component of FIG. 18;

DETAILED DESCRIPTION

Figure 22:
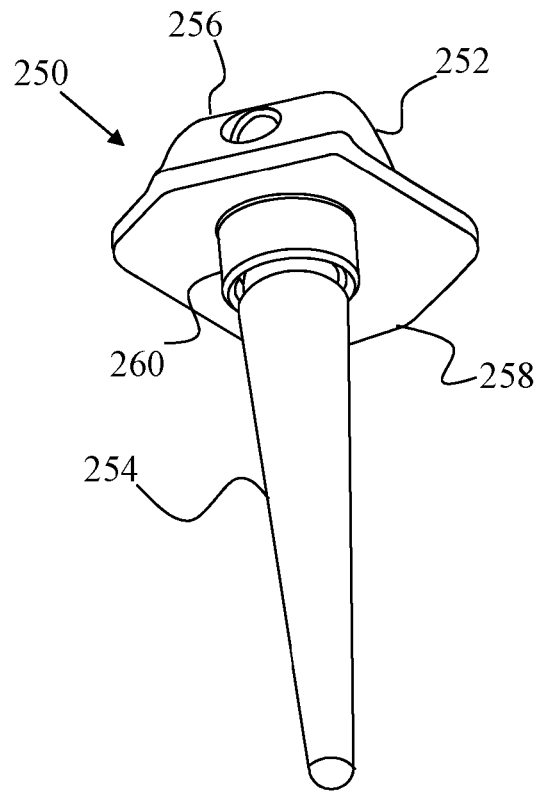
FIG. 22 depicts a bottom perspective of a talar implant including an articulation component directly coupled to a distal portion in accordance with principles of the present invention.

FIG. 1 shows a talar implant 100. The talar implant 100 includes a distal portion 102, an articulating component 104 and a base 106. The distal portion 102 includes a stem 108 which terminates at a shoulder 110. A head 112 is spaced apart from the shoulder 110 by a neck 114 as shown in FIG. 2. The head 112 is generally spherical.

The articulating component 104 includes a generally domed shape articulation surface 120 which is configured to articulate with the tibial component (not shown) of the talar implant system. Two platforms 122 and 124 extend outwardly from the articulation surface 120 as shown in FIG. 3. The articulating component 104 further includes a tool coupler portion 126 and a female coupler 128. The tool coupler portion 126 is configured to couple with an insertion tool (not shown) to assist in positioning the articulating component 104. The female coupler 128, which in this embodiment is a dovetail coupler component, includes an entry 130. The female coupler 128 includes an inner surface 132 extending from the entry 130.

The base 106 includes a male coupler 134 and a female coupler 136. The male coupler 134 is configured to be received into the dovetail receiving portion 128 to provide a dovetail coupling between the articulating component 104 and the base 106. The male coupler 134 includes a threaded bore 138. The bore 138, which is configured to receive a fastener 140. The female coupler 136 includes a mouth 142 that opens to a cylindrical internal bore 144. In alternative embodiments, the female coupler 136 may be provided with a tapered bore which has a diameter which decreases in a direction from the mouth 142 to the male coupler 134.

Assembly of the talar implant 100 may begin with the selection of an articulating component 104. A kit may include articulating components 104 with a variety of differently shaped and sized articulating surfaces 120. The articulating component 104 is then assembled with the base 106 by aligning the male coupler 134 of the base 106 with the entry 130 of the female coupler 128 of the selected articulating component 104 and inserting the male coupler 134 into the female coupler 128 in the direction of the arrow 146 in FIG. 4. As the male coupler 134 is fully inserted into the female coupler 128, the male coupler 134 and the female coupler 128 frictionally engage thereby rigidly coupling the base 106 and the articulating component 104. Additionally, the bore 138 exposes a portion of the surface 132 as shown in FIG. 5.

Next, the fastener 140 may be threaded through the bore 138 and forced against the surface 132 ensuring rigid coupling of the base 106 and the articulating component 104 as shown in FIG. 6. The rigidly coupled base 106 and articulating component 104 may then be coupled with the distal portion 102. Coupling is accomplished by aligning the mouth 142 with the head 112 and moving the rigidly coupled base 106 and articulating component 104 in the direction of the arrow 148.

The head 112 has a diameter that is larger than the diameter of the cylindrical internal bore 144. Accordingly, as the head 112 is inserted into the internal bore 144, the head 112 frictionally engages the inner wall of the internal bore 144. Thus, the distal portion 102 is coupled to the base 106 as shown in FIG. 7. If desired, an even firmer coupling may be achieved by impacting the base 106 onto the head 112. The stem 108, which may include a coating or surface feature for achieving a solid attachment with a bone, may then be inserted into a prepared bone (not shown). An insertion tool (not shown) may be used for placement of the talar implant 100 by coupling the tool with the talar implant 100 using the tool coupler 126.

A number of variations to the procedure set forth above may be made. For example, the distal portion 102 may be implanted into a prepared bone or bones prior to coupling of the distal portion 102 with the base 106. This variation is facilitated by the manner in which coupling is achieved between the base 106 and the distal portion 102. Specifically, FIG. 8 shows a partial cross-sectional view of the distal portion 102 coupled with the base 106. The head 112 is circularly shaped. Accordingly, regardless of the orientation of the head 112 within the internal bore 144, a rigid coupling may be produced so long as the head 112 is properly sized with respect to the internal bore 144.

Moreover, the shoulder 110 is spaced apart from the head 112 by the neck 114. Thus, when the longitudinal axis of the distal portion 102 is perpendicular to the plane of the base 106, the shoulder 110 is spaced apart from the mouth 142 of the female coupler 136 as shown in FIG. 8. Accordingly, a rigid coupling of the head 112 within the internal bore 144 may be produced even when the longitudinal axis of the distal portion 102 is not perpendicular to the plane of the base 106. For example, FIG. 9 shows the distal portion 102 extending downwardly and to the left of the plane of the base 106 while FIG. 10 shows the distal portion 102 extending downwardly and to the right of the plane of the base 106. The amount of angulation between the distal portion 102 and the base 106 that is available is a function of the length and diameter of the neck 114.

Accordingly, while the distal portion 102 may be rigidly coupled to the base 106 such that when viewed in an anterior posterior plane, the longitudinal axis 150 of the distal portion 102 is perpendicular to the plane 152 of the base 106 as shown in FIG. 11, it may also be rigidly coupled to the base 106 such that when viewed in an anterior posterior plane, the longitudinal axis 150 of the distal portion 102 has an anterior cant to the plane 152 of the base 106 as shown in FIG. 12 or a posterior cant as shown in FIG. 13. Additionally, the distal portion 102 may be rigidly coupled to the base 106 at any anterior/posterior angle between the angles shown in FIGS. 12 and 13.

Thus, the angular positions shown in FIGS. 12 and 13 define a plane perpendicular to the plane 152. The distal portion 102 may be coupled to the base 106 at any angular position selected from the set of angles including each angle in the range of angular positions from the angular position shown in FIG. 12 to the angular position shown in FIG. 13 in the anterior/posterior plane perpendicular to the base plane 152.

Moreover, the head 112 may be rigidly coupled to the base 106 such that when viewed in a medial/lateral plane, the longitudinal axis 150 of the distal portion 102 is perpendicular to the plane 152 of the base 106 as shown in FIG. 14, or with a medial cant as shown in FIG. 15 or a lateral cant as shown in FIG. 16. Thus, the angular positions shown in FIGS. 15 and 16 also define a plane perpendicular to the plane 152. The distal portion 102 may be coupled to the base 106 at any angular position selected from the set of angles including each angle in the range of angular positions from the angular position shown in FIG. 15 to the angular position shown in FIG. 16 in the medial/lateral plane perpendicular to the base plane 152.

The combination of all possible orientations at which the distal portion 102 may be coupled to the base 106 thus defines a cone with a vertex at the internal bore 144. Accordingly, the distal portion 102 may be positioned at any orientation within the cone of implantation defined by the physical structure of the base 106 and the distal portion 102. Therefore, if an acceptable portion of a bone or bones exists within the implantation cone for a particular location of the base 106, the talar implant 100 may be firmly implanted in the portion of a bone or bones by selection of the corresponding angular orientation of the distal portion 102 within the implantation cone.

Returning to the present example, once the distal portion 102 is implanted in the selected orientation, the rigidly coupled articulating component 104 and base 106 may be positioned on the head 112 of the distal portion 102 using an insertion tool (not shown) coupled to the tool coupler 126.

The ability to position the distal portion 102 at a variety of angular orientations provides the ability to adapt the talar implant 100 to a wide variety of patient circumstances. In one embodiment, an even wider variety of patient circumstances may be addressed by the provision of a kit including distal portions of different lengths. Furthermore, distal portions may be provided in a variety of shapes to provide for an even greater variety of patient circumstances. By way of example, FIG. 17 depicts a distal portion 160 that may be used with the base 106 of FIG. 1. The distal portion 160 includes a head 162 and a stem 164. The head 162 is configured like the head 112 of the distal portion 102. In contrast to the generally peg-like appearance of the stem 108 of the distal portion 102, however, the stem 164 is more of a four-sided fin shape. The distal portion 160, or other shapes of distal portions, may further be provided in varying lengths.

Referring to FIG. 18-21, an alternative talar implant 200 is shown. The talar implant 200 is configured similarly to the talar implant 100 and includes a distal portion 202, a base 204 and an articulating component 206. The base 204 includes a female coupling portion 208 with a tapered internal bore 210. Additionally, the base 204 includes a guide 212 extending above a male dovetail coupler 214. A threaded bore 216 is located in the guide 212.

The articulating component 206 includes a female dovetail coupler 220, and articulating surface 222 and a tool coupler 224. The female dovetail coupler 220 includes an entry 226 which is located on the side of the articulating component 206 opposite to the location of the tool coupler 224. A channel 228 extends from the entry 226 to a rear wall 230 shown in FIG. 21. A bore 232 which is sized to allow a portion of a fastener 234 (see FIG. 18) to pass therethrough extends between the tool coupler 224 and the channel 228.

The talar implant 200 may be assembled and implanted in the same manner as the talar implant 100. Unlike the talar implant 100, however, the articulating component 206 is rigidly attached to the base 204 by the insertion of the fastener 234 through the tool coupler 224. Accordingly, the base 204 may be coupled with the distal portion 202 prior to coupling of the base 204 to the articulating component 206.

Thus, in an exemplary method, the distal portion 202 is implanted into a bone or bones in accordance with appropriate surgical procedures. Next, the female coupling portion 208 is coupled to the distal portion 202 in a manner similar to that described above with respect to the talar implant 100. Since the articulating component 206 is not coupled to the base 204, the articulating surface 222 cannot be damaged during the coupling of the base 204 and the distal portion 202.

Next, using a tool (not shown) coupled with the articulating component 206 through the tool coupler 224, the channel 228 is aligned with the guide 212 and the entry 226 of the female dovetail coupler 220 is aligned with the male dovetail coupler 214. The articulating component 206 is then slid into position on the base 204 with the dovetail coupler 214 contacting the rear wall 230 and the insertion tool is removed. As the male dovetail coupler 214 comes into contact with the rear wall 230, the guide 212 and channel 228 ensure that the bore 216 aligns with the bore 232.

Removal of the insertion tool allows the fastener 234 to be inserted into the tool coupler 224 and the shaft of the fastener 234 is inserted through the bore 232 and into the aligned bore 216. The fastener is then used to rigidly couple the articulating component 206 with the base 204.

The provision of access to the fastener 234 through the tool coupler 224 allows for simple replacement of the articulating component 206. Specifically, the distal portion 202 need not be disturbed and the base 204 need not be decoupled from the distal portion 202. Rather, once access to the tool coupler 224 is provided through an incision, the fastener 234 is removed through the tool coupler 224 and out of the patient through the incision. Thereafter, an insertion tool may be coupled to the articulating component 206 using the tool coupler 224. The articulating component 206 may then be removed by moving the articulating component 206 away from the base 204 and out through the incision. Replacement of the articulating component 206 with a new articulating component is then performed in the same manner described above.

Thus, the articulating component 206 may be replaced without disturbing the distal portion 202 or the base 204. Moreover, since access to the fastener 234 is through the tool coupler 224, a single small incision may be used when replacing the articulating component 206.

An alternative talar implant 250 is shown in FIG. 22. The talar implant 250 includes an articulating component 252 and a distal portion 254. The articulation component 252 includes an articulating surface 256 and a base 258. The base 258 extends along a plane from which the articulating surface extends in an upwardly direction. A female coupler 260 extends downwardly from the base 258. The female coupler 260 and the distal portion 254 are coupled in the same manner as the female coupler 136 and the distal portion 102. The talar implant 250 is thus similar to the talar implant 100. The main difference is that the base 258 is integrally formed with the articulating component 252.

Figure 23:
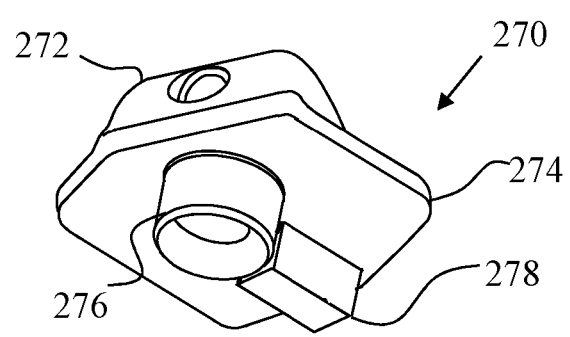
FIG. 23 depicts a bottom perspective view of an articulation component with a base including a cylindrical coupler portion and a protuberance in the form of a fin component in accordance with principles of the present invention.

The components described above may be included in a kit to provide a surgeon with flexibility in determining the best combination of components for a particular patient. Additional components may be provided in a kit to allow for even greater flexibility. For example, the articulation component 270 shown in FIG. 23 may be provided in a kit with the components discussed above. The articulation component 270 includes an articulating surface 272 and an integrally formed base 274. Additionally, a female coupler 276 extends from the base 274 which may be used to rigidly couple the articulation component 270 with a distal portion such as the distal portion 102 or the distal portion 160.

The articulation component 270 further includes a fin 278. The fin 278, which may be provided generally aligned with the articulating surface 272 or in another desired alignment, protrudes downwardly form the base 274 and provides increased resistance to rotational movement of the articulation component 270.

Figure 24:
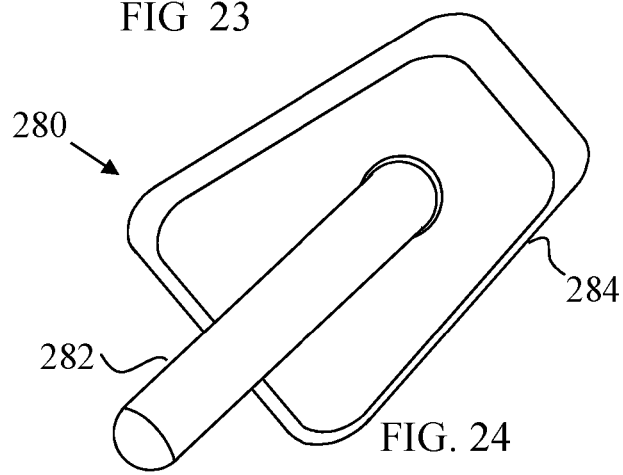
FIG. 24 depicts a bottom perspective view of a distal portion incorporating a stem and a dovetail coupler portion in accordance with principles of the present invention.
Figure 25:
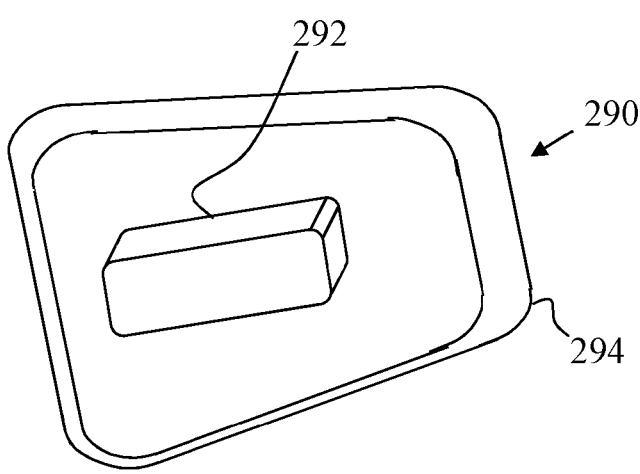
FIG. 25 depicts a bottom perspective view of a distal portion incorporating a protuberance in the form of a fin and a dovetail coupler portion in accordance with principles of the present invention.

A kit may further include a distal portion 280 that includes a stem 282 and a dovetail coupler 284 as shown in FIG. 24. The dovetail coupler 284 may be used to rigidly couple the anchor portion 280 with the articulation component 104 of FIG. 1. The distal portion 290 shown in FIG. 25 may also be included in the kit. The distal portion 290 includes a fin 292 and a dovetail coupler 294. The dovetail coupler 294 may be used to rigidly couple the distal portion 290 with the articulation component 104 of FIG. 1.

While the present invention has been illustrated by the description of exemplary processes and system components, and while the various processes and components have been described in considerable detail, the applicants do not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of the applicants' general inventive concept.

I claim:

1. A method of implanting a permanent talar implant assembly including an articulation component, a base member with a cylindrical bore, and a distal portion with a solid spherical head, the method comprising:
   providing the articulation component;
   providing the base member;
   providing the distal portion;
   coupling the provided articulation component having an articulating surface extending upwardly from a first plane to an apex and then downwardly toward the first plane, and configured to articulate with a tibial prosthetic device, with the provided base member, at least one of the provided articulation component and the provided base member having a planar portion defining the first plane;
   selecting an angular position for a longitudinal axis of the provided distal portion with respect to the first plane from a range of angular positions within a second plane perpendicular to the first plane, wherein the solid spherical head and the cylindrical bore are configured to allow the solid spherical head to be positioned in the cylindrical bore at any of a plurality of relative orientations, of the solid spherical head and the cylindrical bore, which define the range of angular positions and the provided distal portion and the provided base member are couplable at each of a plurality of angular positions within the range of angular positions;
   orienting the provided distal portion with the provided base member at the selected angular position with the solid spherical head at least partially within the cylindrical bore;
   rigidly frictionally coupling the oriented provided distal portion with the provided base member at the selected angular position with a rigid friction coupling sufficient for permanent implantation of the permanent talar implant assembly; and implanting the provided distal portion in at least one bone of a foot.

2. The method of claim 1, wherein coupling the provided articulation component with the provided base member is performed after implanting the provided distal portion.

3. The method of claim 2, wherein rigidly frictionally coupling the provided distal portion with the provided base member is performed before coupling the provided articulation component with the provided base member.

4. The method of claim 1, wherein coupling the provided articulation component with the provided base member comprises coupling the provided articulation component with the provided base member using a dovetail configuration.

5. The method of claim 4, further comprising:
inserting a portion of a fastener through a tool coupler in the provided articulation component; and
inserting the portion of the fastener into a bore in the provided base member.

6. The method of claim 5, further comprising:
coupling an insertion tool with the tool coupler of the provided articulation component, wherein orienting the provided distal portion with the provided base member at the selected angular position comprises:
positioning the provided articulation component using the coupled insertion tool.

7. The method of claim 6, wherein:
the tool coupler opens to a posterior surface portion of the provided articulation component; and
coupling an insertion tool with the tool coupler comprises inserting the insertion tool into the posteriorly opening tool coupler.

8. The method of claim 1, further comprising:
inserting a fin extending from the provided base member away from the first plane into the at least one bone of the foot.

9. The method of claim 1, wherein:
the cylindrical bore has a first diameter;
the spherical head has a second diameter, the second diameter larger than the first diameter; and
insertion alone of the spherical head into the cylindrical bore produces the rigid friction coupling sufficient for a permanent talar implant assembly.

10. The method of claim 1, further comprising:
selecting the provided articulation component from a plurality of provided articulation components, each of the plurality of provided articulation components having a surface configured to articulate with a tibial prosthetic device.

11. The method of claim 1, wherein implanting the provided distal portion in at least one bone of the foot is accomplished prior to orienting the provided distal portion with the provided base member at the selected angular position with the solid spherical head at least partially within the cylindrical bore.

* * * * *